(12) United States Patent  
Chen

(10) Patent No.: US 8,297,749 B2  
(45) Date of Patent: Oct. 30, 2012

(54) GLASSES CONSTRUCTION

(75) Inventor: Chun-Nan Chen, Tainan (TW)

(73) Assignee: Bor Jye Enterprise Co., Ltd., Tainan (TW)

( * ) Notice: Subject to any disclaimer, the term of this patent is extended or adjusted under 35 U.S.C. 154(b) by 129 days.

(21) Appl. No.: 12/960,608

(22) Filed: Dec. 6, 2010

(65) Prior Publication Data

US 2012/0140162 A1    Jun. 7, 2012

(51) Int. Cl.
 *G02C 7/08* (2006.01)
(52) U.S. Cl. ............... 351/57; 351/44; 351/62; 351/140
(58) Field of Classification Search .................. 351/41, 351/44, 47–48, 57–58, 62, 140; 2/426, 439, 2/442–445, 448, 450
See application file for complete search history.

(56) References Cited

U.S. PATENT DOCUMENTS

| 7,062,798 B2 | 6/2006 | Wu | |
| 7,396,124 B1 * | 7/2008 | Wang | 351/47 |
| 7,419,260 B1 * | 9/2008 | Wang | 351/156 |

* cited by examiner

*Primary Examiner* — Huy K Mai
(74) *Attorney, Agent, or Firm* — Alan Kamrath; Kamrath IP Lawfirm, PA

(57) ABSTRACT

A glasses construction includes an auxiliary frame coupled with optical lenses and disposed as needed behind the middle portion of a glasses frame coupled with lenses; and a protective frame disposed behind and snap-engaged with the glasses frame. The glasses frame and the protective frame together limit the position of the auxiliary frame. Two connecting elements, pivotally disposed on two sides of the glasses frame, respectively, are snap-engaged with connecting members extending from the ends of two temples and stopping portions formed beside the connecting members to thereby form a glasses construction. Hence, the combination or separation between the glasses frame and the protective frame, between the glasses frame and the auxiliary frame, or between the two connecting elements pivotally disposed on two sides of the glasses frame and the temples is advantageously characterized by quick positioning or removal by convenient operation.

4 Claims, 5 Drawing Sheets

GLASSES CONSTRUCTION

FIELD OF THE INVENTION

The present invention relates to glasses constructions and, more particularly, to a glasses construction for use in sports. The glasses construction for use in sports comprises a glasses frame and a protective frame disposed behind the glasses frame. Upon directional engagement with each other, the glasses frame and the protective frame together effectuate the quick and stable positioning thereof. In an embodiment with enhanced ease of use, the glasses construction further comprises, as needed, an auxiliary frame coupled with optical lenses, and temples disposed on the two sides of the glasses frame. Thus, a wearer is able to operate the glasses construction conveniently, thereby allowing the glasses construction to be, upon directional engagement or when dismounted, precisely worn by or removed from the wearer, and facilitating the replacement of a strap with one of a different shape.

BACKGROUND OF THE INVENTION

A conventional glasses construction for use in sports usually comprises: a glasses frame coupled with two lenses; a protective frame mounted on an inner side of the glasses frame and configured to protect the wearer's nose and forehead; and temples and/or a strap disposed on two sides of the glasses frame, respectively, for the wearer to choose from as needed during sports. U.S. Pat. No. 7,062,798B2, entitled GLASSES HAVING A PROTECTIVE MODULE, and issued on Jun. 20, 2006, discloses a pair of sports glasses coupled with a fastening strap. The fastening strap is mounted on two sides of the sports glasses and has two ends each coupled with a connecting element. Snapping portions which are directed outward are formed on two opposite sides of the sports glasses. Locking bosses are formed on two sides of the connecting members, respectively. Positioning holes are formed at the ends of the left and right temples pivotally connected to the sports glasses and positioned proximate to intersections of the glasses frame. Upper and lower holes are concavely disposed on the inner surface of the locking holes positioned proximate to the left and right temples, such that the locking holes receive the snapping portions positioned proximate to the connecting elements at the two ends of the fastening strap respectively during an assembly process. The locking bosses positioned proximate to the connecting members are forced into a plurality of receiving holes of the temples, respectively. Each of the two snapping portions of the connecting members of the fastening strap is locked in a respective one of the two locking holes of the respective temple, so that the fastening strap is mounted on the sports glasses rigidly and stably by snap-in engagement.

BRIEF SUMMARY OF THE INVENTION

The present invention improves on the conventional glasses construction for use in sports such that the glasses construction of the present invention comprises a glasses frame and a protective frame disposed behind the glasses frame. Upon directional engagement with each other, the glasses frame and the protective frame together effectuate the quick and stable positioning thereof. In an embodiment with enhanced ease of use, the glasses construction further comprises, as needed, an auxiliary frame coupled with optical lenses, and temples disposed on the two sides of the glasses frame, such that a wearer is able to operate the glasses construction conveniently, thereby allowing the glasses construction to be, upon directional engagement or when dismounted, precisely positioned or removed from the wearer for replacing the strap with one of a different shape.

It is a primary objective of the present invention to provide a glasses construction for use in sports. The glasses construction comprises: a glasses frame coupled with lenses; a protective frame disposed behind the glasses frame; an auxiliary frame sandwiched between the glasses frame and the protective frame and coupled with optical lenses; two connecting elements pivotally disposed on two sides of the glasses frame, respectively; and temples each disposed at one end of a corresponding one of two said connecting elements. The glasses frame is characterized by: a receiving space formed on an outer side of a frame rim holding a corresponding one of the lenses; and a notch disposed at the margin of the receiving space. Hook portions extending forward from two opposing outer sides of the protective frame corresponding in shape to the glasses frame are inserted into the receiving spaces. Abutting portions formed on the inner sides of the hook portions are inserted into the notches, respectively. A downward-facing abutting space is formed at the middle portion of the protective frame. Upon engagement of the protective frame and the glasses frame, a corresponding portion of the rim of the glasses frame is inserted into the abutting space. As a result, a convenient operation whereby the glasses frame is mounted on or dismounted from the protective frame is advantageously characterized by stable positioning or separation.

The second objective of the present invention is to provide a glasses construction. The glasses frame of the glasses construction is further characterized by: a recess portion formed on an inner side of the frame rim holding a corresponding one of the lenses; and a groove oriented in a preset direction and disposed on an inward side at the middle portion of the glasses frame. An engaging portion extending forward from the middle portion of the auxiliary frame coupled with the optical lenses is inserted into the groove of the glasses frame. Two opposing protruding portions extend from the middle portion of the auxiliary frame in a manner that the protruding portions abut against the recess portions of the glasses frame, respectively. The position of the rear side of the auxiliary frame is limited by the protective frame, and, thus, the auxiliary frame can be precisely positioned or removed when mounted or dismounted by simple implementation.

The third objective of the present invention is that the nasal portions of the left and right frames of the protective frame disposed behind the glasses frame are bent inward and thinned such that, upon directional engagement of the glasses frame and the protective frame, the nasal portions of the left and right frames of the protective frame are spaced apart from the glasses frame. As a result, nasal pads extending from the glasses frame impose a directional limitation upon the nasal portions of the left and right frames of the protective frame, thereby allowing the protective frame and the glasses frame to abut against each other centrally and appropriately.

The fourth objective of the present invention is that the two connecting elements are pivotally coupled to the two outer sides of the glasses frame, respectively, are formed therein with and are penetrated by a via disposed rearward, and are centrally formed with a through-hole communicating with the via. Resilient stopping portions formed at the connecting members to extend toward the temples and extend inward, respectively, can be snap-engaged with the through-holes centrally formed in two said connecting elements, respectively, after the connecting members are inserted into the vias of two said connecting elements. Hence, a wearer is able to quickly operate the two connecting elements pivotally disposed on the two sides of the glasses frame, thereby allowing the two connecting elements to be precisely positioned at or removed from the temples upon directional engagement with or when dismounted from the temples, respectively, so a strap can be replaced with one of a different shape.

DETAILED DESCRIPTION OF THE EMBODIMENTS OF THE INVENTION

Figures 1, 1A, 1B:
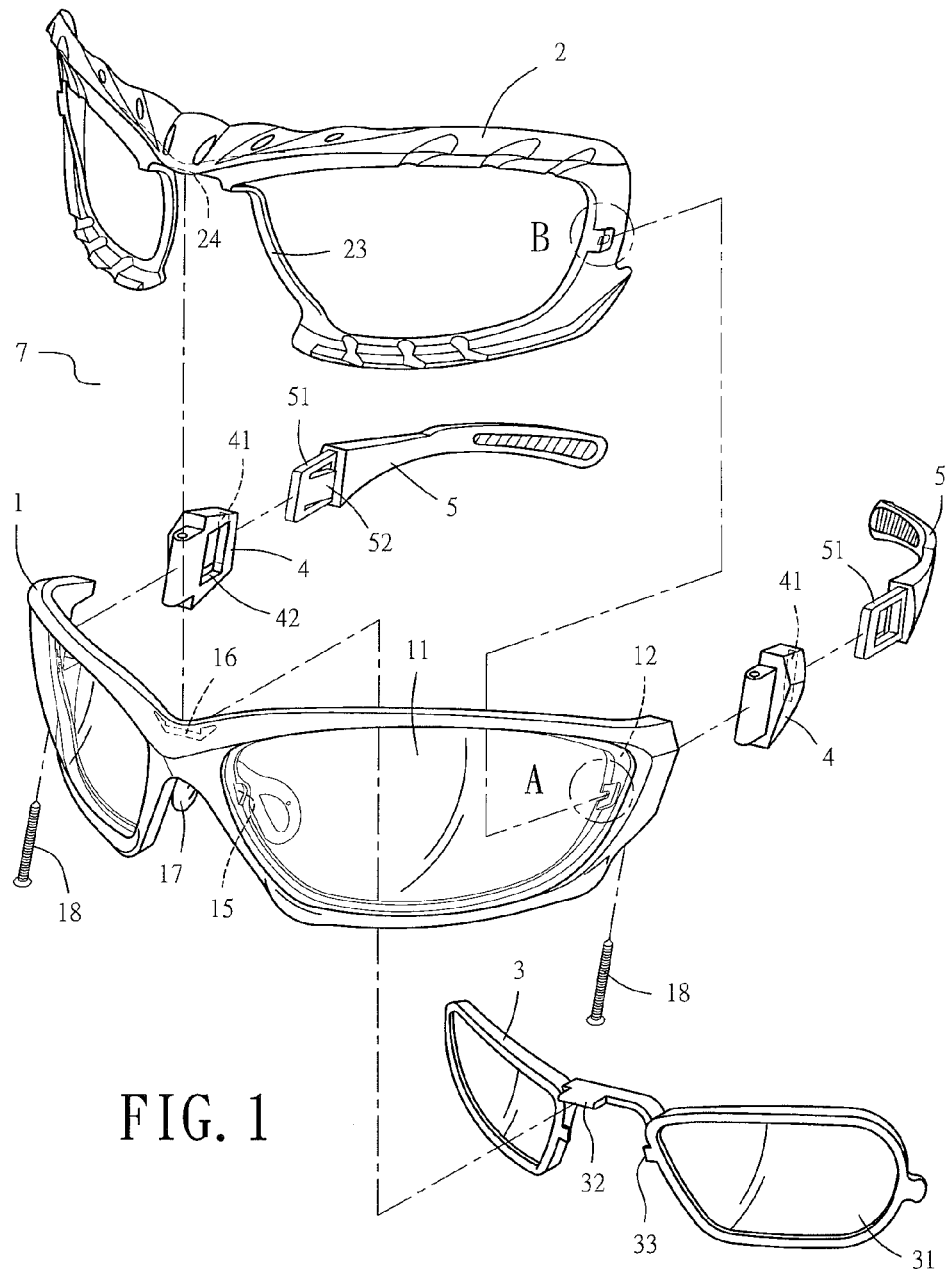
FIG. 1 is a schematic exploded view of a glasses construction according to a first embodiment of the present invention.
FIG. 1A is an enlarged view of portion A in FIG. 1.
FIG. 1B is an enlarged view of portion B in FIG. 1.

The present invention provides a glasses construction 7 (see FIG. 1) for use in sports. The glasses construction 7 comprises: a glasses frame 1 coupled with lenses 11; a protective frame 2 disposed behind the glasses frame 1; an auxiliary frame 3 sandwiched between the glasses frame 1 and the protective frame 2 and coupled with optical lenses 31; two connecting elements 4 pivotally disposed on the two sides of the glasses frame 1, respectively; and temples 5 each disposed at one end of a corresponding one of the two connecting elements 4.

The glasses frame 1 is characterized by: a receiving space 13 formed on an outer side of a frame rim 12 holding a corresponding one of the lenses 11; a notch 14 disposed at the margin of the receiving space 13; a recess portion 15 formed on an inner side of the frame rim 12 holding a corresponding one of the lenses 11; a groove 16 oriented in a preset direction (i.e., in an obliquely upward direction in this embodiment) and disposed on an inward side at the middle portion of the glasses frame 1; and nasal pads 17 extending inward from the glasses frame 1 bilaterally.

The protective frame 2 is characterized by: rear protective elements corresponding in position to left and right frames of the glasses frame 1, with a flexible protective element (not shown) which is made of EVA coupled to the protective frame 2 from the back thereof; two hook portions 21 extending forward from two opposing outer sides of the protective frame 2, respectively; an abutting portion 22 formed on an inner side of the hook portion 21, with the nasal portions of the left and right frames 23 of the protective frame 2 bent inward and thinned; and a downward-facing abutting space 24 formed at the middle portion of the protective frame 2.

The auxiliary frame 3 is characterized by: an engaging portion 32 extending forward from the middle portion of the auxiliary frame 3 coupled with the optical lenses 31; and two protruding portions 33 extending from the middle portion of the auxiliary frame 3 in a manner that the protruding portions 33 point at each other.

The two connecting elements 4 are pivotally coupled to the two outer sides of the glasses frame 1 by two screwing elements 18, respectively, are formed therein with and penetrated by a via 41 disposed rearward, and are centrally formed with a through-hole 42 communicating with the via 41.

The two temples 5 are characterized by: a connecting member 51 extending from the front end of each of the two temples 5; and a resilient stopping portion 52 formed on one side of the connecting member 51 to extend toward the corresponding one of the two temples 5 and extend inward.

Figure 2:
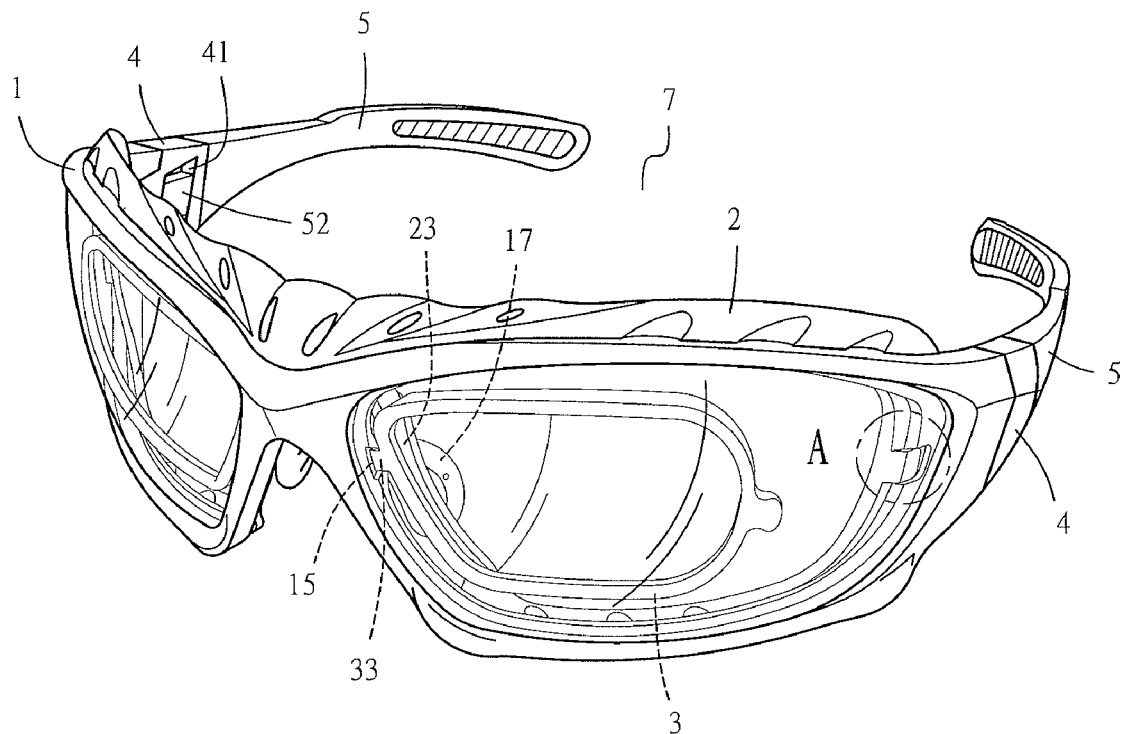
FIG. 2 is a schematic perspective view of the glasses construction according to the present invention.

To put together the glasses frame 1, the protective frame 2, the auxiliary frame 3, the connecting elements 4 pivotally disposed on the two sides of the glasses frame 1, respectively, and the temples 5 to implement the glasses construction 7 of the present invention (as shown in FIG. 2), a wearer inserts the engaging portion 32 extending forward from the middle portion of the auxiliary frame 3 coupled with the optical lenses 31 into the groove 16 of the glasses frame 1. The two protruding portions 33 pointing at each other and extending from the middle portion of the auxiliary frame 3 abut against the recess portions 15 of the glasses frame 1, respectively.

Figure 2A:
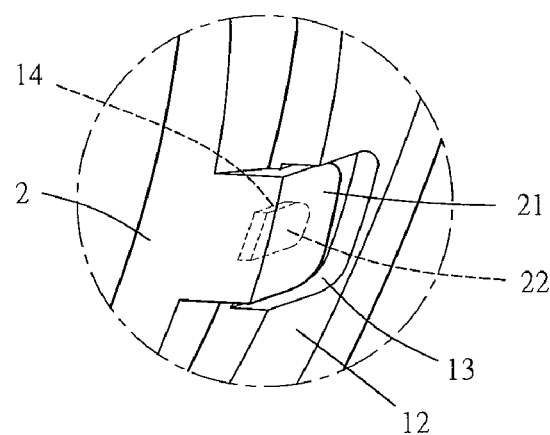
FIG. 2A is an enlarged view of portion A in FIG. 2.
Figure 3:
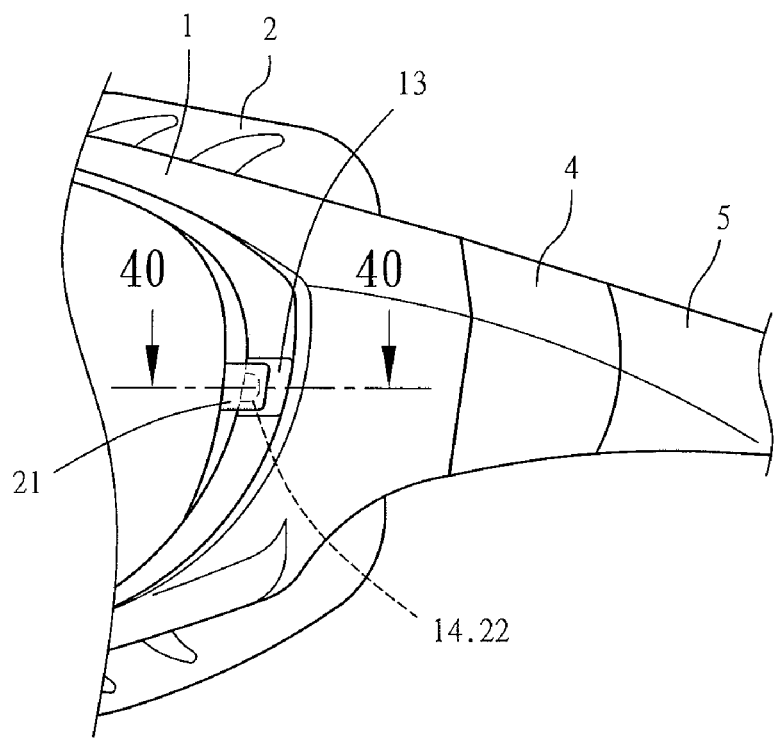
FIG. 3 is a schematic partial side view of the glasses construction according to the present invention.
Figure 4:
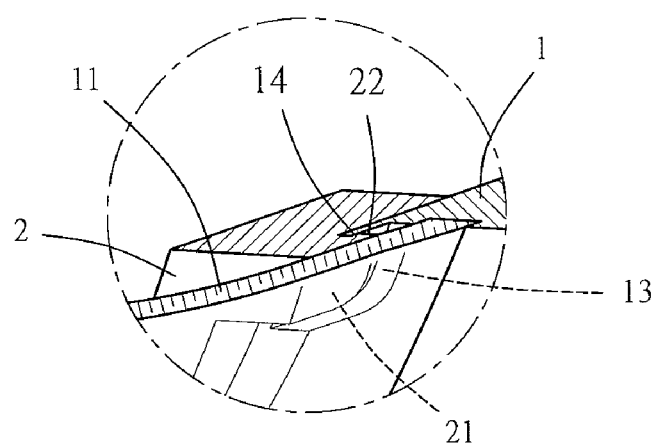
FIG. 4 is a cross-sectional view taken along line 40-40 of FIG. 3.

Afterward, the wearer inserts the hook portions 21 extending forward from two opposing outer sides of the protective frame 2 into the receiving spaces 13 formed on the outer sides of the frame rims 12 of the glasses frame 1, respectively (as shown in FIG. 2A and FIG. 3), inserts the abutting portions 22 formed on the inner sides of the hook portions 21 into the notches 14, respectively (as shown in FIG. 3 and FIG. 4), and positions the downward-facing abutting space 24 formed at the middle portion of the protective frame 2 in a manner that the abutting space 24 corresponds in position to the upper rim of the glasses frame 1 (as shown in FIG. 2). The protective frame 2 limits the position of the auxiliary frame 3 from behind, such that the auxiliary frame 3 can be precisely positioned or removed as needed upon engagement with or when dismounted from the protective frame 2 by simple implement. Also, the wearer can mount/dismount the glasses frame 1 and the protective frame 2 easily, such that their positioning and/or removal can be performed steadily.

The inwardly bent and thinned nasal portions of the left and right frames 23 of the protective frame 2 are spaced apart from corresponding portions of the glasses frame 1 by a distance (shown in FIG. 2 and configured to allow the auxiliary frame 3 to be coupled therebetween). The position of the thinned nasal portions of the left and right frames 23 of the protective frame 2 are limited by the two nasal pads 17 extending from the glasses frame 1, such that the protective frame 2 abuts against the middle portion of the glasses frame 1 appropriately.

Afterward, the wearer inserts the connecting members 51 extending from the front ends of the temples 5 into the vias 41 of the connecting elements 4 pivotally coupled to the glasses frame 1, respectively (as shown in FIG. 2), and enables snap-engagement between the stopping portions 52 formed on the connecting members 51 and the through-holes 42 centrally formed in the connecting elements 4, respectively (as shown in FIG. 2). Thus, the two temples 5 can be snap-engaged with and/or removed from the connecting elements 4 pivotally coupled to the two outer sides of the glasses frame 1, thereby allowing the glasses construction 7 to be quickly operated by the wearer and thus precisely positioned or removed from the wearer for replacing the temples 5 with ones of a different shape and/or for replacing a strap with one of a different shape (as disclosed in the embodiment illustrated with FIG. 5 and FIG. 6 below).

Figure 5:
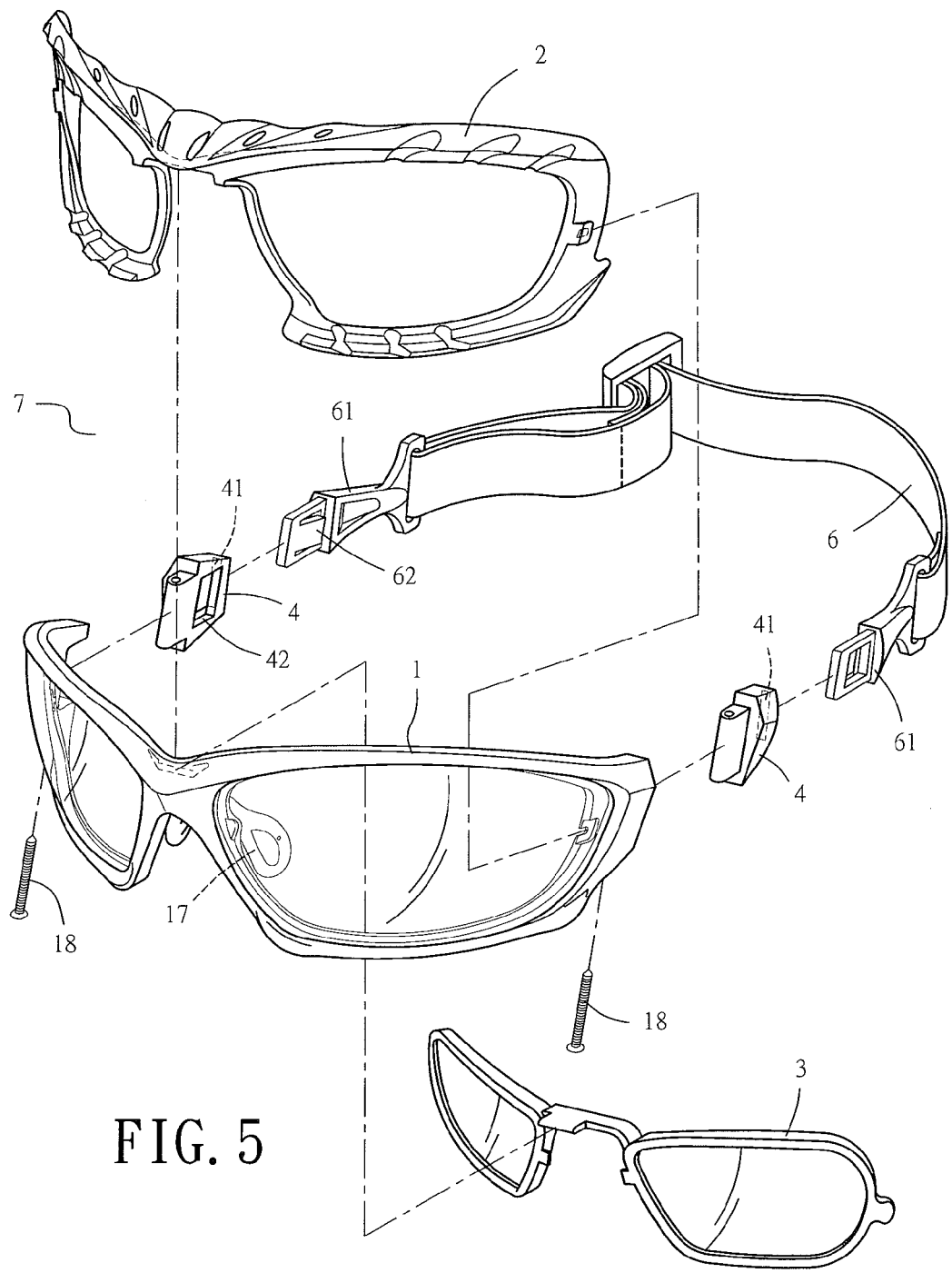
FIG. 5 is a schematic exploded view of the glasses construction according to a second embodiment of the present invention.

In a second embodiment (as shown in FIG. 5) of the present invention, the glasses construction 7 comprises: the glasses frame 1 coupled with the lenses 11; the protective frame 2 disposed behind the glasses frame 1; the auxiliary frame 3 sandwiched between the glasses frame 1 and the protective frame 2 and coupled with the optical lenses 31; the connecting elements 4 pivotally disposed on the two sides of the glasses frame 1, respectively; and a strap 6 fastened to one end of each of the connecting elements 4. The second embodiment is the same as the first embodiment (illustrated with FIG. 1) in terms of constituent elements except that in the second embodiment, the two ends of the strap 6 are coupled to a connecting member 61, and a resilient stopping portion 62 is formed at the connecting member 61 to extend inward and backward.

Figure 6:
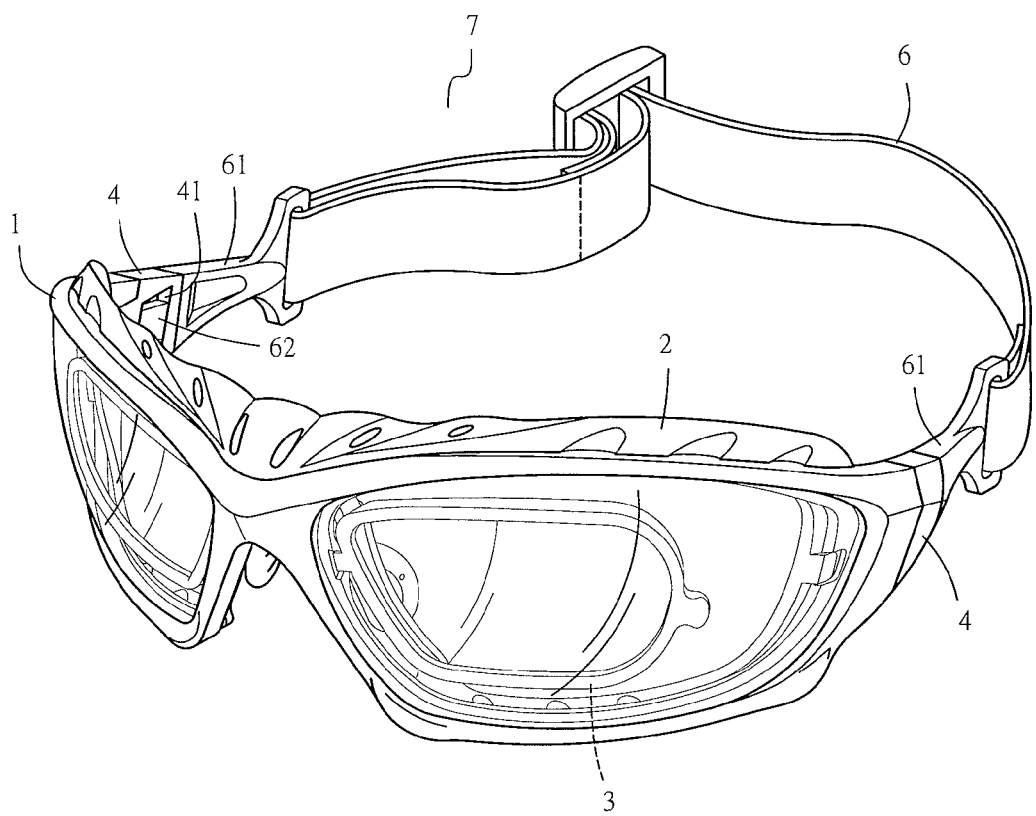
FIG. 6 is a schematic perspective view of the glasses construction according to the second embodiment of the present invention.

To fasten the strap 6 to the connecting elements 4 pivotally disposed on the two sides of the glasses frame 1 of the glasses construction 7 (as shown in FIG. 6), the wearer inserts the connecting members 61 coupled to the two ends of the strap 6 into the vias 41 formed in the connecting elements 4 pivotally coupled to the two outer sides of the glasses frame 1. Snap-engagement is enabled between the stopping portions 62 formed on the connecting members 61 and the through-holes 42 centrally formed in the connecting elements 4, respectively. Hence, the connecting elements 4 pivotally disposed on the two sides of the glasses frame 1 can be switched between the strap 6 in the second embodiment and the temples 5 in the first embodiment flexibly and quickly.

What is claimed is:

1. A glasses construction, comprising:
a glasses frame including a frame rim holding lenses; a protective frame corresponding in shape to and disposed behind the glasses frame; an auxiliary frame sandwiched between the glasses frame and the protective frame and coupled with optical lenses; two connecting elements pivotally disposed on two sides of the glasses frame, respectively; and temples each disposed at an end of a corresponding one of the two connecting elements; wherein receiving spaces are formed on outer sides of the frame rim; wherein a notch is disposed in the frame rim at a margin of each receiving space, wherein hook portions extending forward from two opposing outer sides of the protective frame are inserted into the receiving spaces, wherein abutting portions formed on inner sides of the hook portions are inserted into the notches, respectively, wherein a downward-facing abutting space is formed at a middle portion of the protective frame, wherein upon engagement of the protective frame and the glasses frame, a corresponding portion of the frame rim of the glasses frame is inserted into the abutting space, and thus a convenient operation whereby the glasses frame is mounted on or dismounted from the protective frame is advantageously characterized by stable positioning or separation.

2. The glasses construction of claim 1, wherein the recess portions are formed on inner sides of the frame rim holding the lenses; wherein a groove is disposed on an inward side at a middle portion of the glasses frame, wherein an engaging portion extending forward from the middle portion of the auxiliary frame is inserted into the groove of the glasses frame, wherein two opposing protruding portions extend from the middle portion of the auxiliary frame and abut against the recess portions of the glasses frame, respectively, wherein a rear side of the auxiliary frame is limited by the protective frame, wherein the auxiliary frame is precisely positioned or removed when mounted or dismounted.

3. The glasses construction of claim 1, wherein nasal portions of left and right frames of the protective frame disposed behind the glasses frame are bent inward and thinned, wherein upon directional engagement of the glasses frame and the protective frame, the protective frame is centrally spaced apart from the glasses frame, wherein nasal pads extending from the glasses frame impose a directional limitation upon the nasal portions of the left and right frames of the protective frame, allowing the protective frame and the glasses frame to abut against each other centrally.

4. The glasses construction of claim 1, wherein the two connecting elements are each formed therein with and penetrated by a via disposed rearward and are centrally formed with a through-hole communicating with the via, wherein resilient stopping portions, formed at the two connecting members to extend toward the temples and extend inward, respectively, are snap-engaged with the through-holes centrally formed in the two connecting elements, respectively, after the connecting members are inserted into the vias of the two connecting elements, with the two connecting elements pivotally disposed on the two sides of the glasses frame and the two temples disposed on the two sides of the glasses frame, wherein a wearer is able to operate the glasses construction, thereby allowing the glasses construction to be, upon directional engagement or when dismounted, precisely worn by or removed from the wearer, and facilitating replacement of a strap with one of a different shape.

* * * * *